United States Patent

Fisher et al.

Patent Number: 5,407,938
Date of Patent: Apr. 18, 1995

[54] CERTAIN 1-METHYL-PIPERIDINE-4-SPIRO-4'-(1'-3'-OXAZOLINES) AND CORRESPONDING -(1',3' THIAZOLINES)

[75] Inventors: Abraham Fisher, Holon; Yoffi Segall, Ramat Hasharon; Ezra Shirin, Tel Aviv; Yishai Karton, Ness Ziona; Haim Meshulam, Bat Yam, all of Israel

[73] Assignee: Israel Institute for Biological Research, Ness Ziona, Israel

[21] Appl. No.: 137,690

[22] Filed: Oct. 14, 1993

Related U.S. Application Data

[63] Continuation of Ser. No. 685,397, Apr. 9, 1991, abandoned, which is a continuation-in-part of Ser. No. 507,708, Apr. 10, 1990, abandoned.

[51] Int. Cl.⁶ .............. A61K 31/44; C07D 491/20; C07D 495/20; C07D 497/20
[52] U.S. Cl. ........................... 514/278; 546/19
[58] Field of Search .................... 546/19; 514/278

[56] References Cited

U.S. PATENT DOCUMENTS

| | | | |
|---|---|---|---|
| 3,629,276 | 12/1971 | Harnden | 548/216 |
| 3,717,634 | 2/1973 | Wu et al. | 544/230 |
| 3,792,053 | 2/1974 | Potoski et al. | 546/133 |
| 4,083,985 | 4/1978 | Cohen et al. | 514/278 |
| 4,104,397 | 8/1978 | Cohen et al. | 514/278 |
| 4,735,944 | 4/1988 | Bolliger et al. | 514/278 |
| 4,855,290 | 8/1989 | Fisher et al. | 514/278 |
| 4,876,620 | 10/1989 | Fisher et al. | 514/278 |
| 4,900,830 | 2/1990 | Fisher et al. | 546/18 |
| 4,981,858 | 1/1991 | Fisher et al. | 514/278 |

FOREIGN PATENT DOCUMENTS

| | | | |
|---|---|---|---|
| 0205247 | 12/1986 | European Pat. Off. | 514/278 |
| 0239309 | 9/1987 | European Pat. Off. | 546/133 |
| 0311313 | 4/1989 | European Pat. Off. | 514/278 |
| 0337547 | 10/1989 | European Pat. Off. | 514/278 |
| 0350118 | 1/1990 | European Pat. Off. | |
| 2146962 | 3/1973 | France | 546/18 |
| 2331343 | 6/1977 | France | 514/278 |
| 75166 | 5/1989 | Israel | 546/133 |
| 1301254 | 12/1972 | United Kingdom | 546/18 |
| 8500171 | 1/1985 | WIPO | 548/408 |

OTHER PUBLICATIONS

Burger Medicinal Chemistry, Second Edition, p. 497 Interscience Publishers, Inc. 1960.
Wade, Organic Chemistry, p. 349 Prentice-Hall pub. 1987.
J. Sanders et al. J. Med. Chem. 30,969–975, 1987.
Jones et al. J. Chem. Soc. (B),1316–1320, 1971.
Hails et al. J. Chem. Soc. (B),1320–1321, 1971.

*Primary Examiner*—Alan L. Rotman
*Attorney, Agent, or Firm*—Darby & Darby

[57] ABSTRACT

The invention relates to compounds (I) for treating diseases of the central and peripheral nervous system, including enantiomers, racemates and acid addition and quaternary salts,

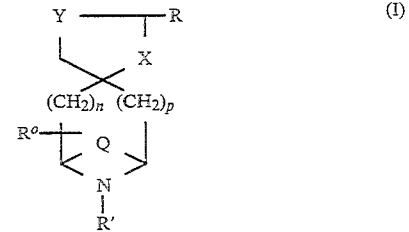

wherein Q is selected from two H atoms, $(CH_2)_m$ and $C(CH_3)_2$ where m is 1, 2 or 3 and n and p are; each independently 0, 1, 2 or 3, provided that $n+p=1-3$, and $R^0$ is H, methyl or OH; the moiety

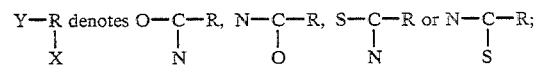

R is selected from H, $NH_2$, $NH-C_{1-6}$-alkyl, $N(C_{1-6}$-alkyl$)_2$, $C_{1-6}$-alkyl, $C_{2-6}$-alkenyl, $C_{2-6}$-alkynyl, $C_{3-7}$-cycloalkyl, $C_{1-6}$-alkyl substituted by 1–6 halogen atoms, hydroxy-$C_{1-6}$-alkyl, $C_{1-6}$-alkoxy, $C_{1-6}$-alkylthio, $C_{1-6}$-alkoxy-$C_{1-6}$-alkyl, carboxy-$C_{1-6}$-alkyl, $(C_{1-6}$-alkoxy)car- (Abstract continued on next page.)

bonyl-$C_{1-6}$-alkyl, amino-$C_{1-6}$-alkyl, mono-($C_{1-6}$-alkyl)amino-$C_{1-6}$-alkyl, di-($C_{1-6}$-alkyl)amino-$C_{1-6}$-alkyl, 2-oxo-pyrrolidin-1-yl-methyl, aryl, diarylmethylol, and $C_{1-6}$-alkyl substituted by one or two aryl groups; R' is independently selected from the group from which R is selected and $C_{1-6}$-alkanoyl and arylcarbonyl; and aryl denotes unsubstituted phenyl or phenyl substituted by 1–3 substituents selected from halogen, $C_{1-6}$-alkyl, $C_{1-6}$-alkoxy and $CF_3$, subject to certain provisos.

4 Claims, No Drawings

CERTAIN 1-METHYL-PIPERIDINE-4-SPIRO-4′-(1′-3′-OXAZOLINES) AND CORRESPONDING -(1′,3′ THIAZOLINES)

This is a continuation of application Ser. No. 07/685,397, filed Apr. 9, 1991, abandoned, which in turn is a continuation-in-part of Ser. No. 07/507,708, filed Apr. 10, 1990, abandoned.

FIELD OF THE INVENTION

The present invention relates to 4- and 5-spiro(1,3-oxazolines 1,3-thiazolines) in which the ring which is spiro-connected to oxazoline or thiazoline is a saturated heterocyclic ring containing one unbridged nitrogen atom; to pharmaceutical compositions containing the spiro compounds and to a method for treating diseases of the central and peripheral nervous system using such spiro-compounds or pharmaceutical compositions.

BACKGROUND OF THE INVENTION

Novel spiro-quinuclidine compounds, in which oxathiolane rings were connected in spiro manner with quinuclidine rings, were described e.g. in European Patent Application No. 0205247 A2, published Dec. 17, 1986, and in U.S. Pat. Nos. 4,855,290 (issued Aug. 8, 1989), No. 4,981,858 (issued Jan. 1, 1991), No. 4,900,830 (issued Feb. 13, 1990) and No. 4,876,620 (issued Oct. 24, 1989), the contents of all of which are incorporated herein by reference. These novel compounds were found to possess central nervous system activity. The biological activity of the compound 2-methylspiro-1,3-oxathiolane-5′,3)quinuclidine, which exists as geometrical cis- and trans-isomers depending upon whether the 2-methyl group is located on the same side of the oxathiolane ring as the quinuclidine ring nitrogen atom (cis) or on the other side of the quinuclidine ring nitrogen atom (trans), was in particular extensively investigated, and it was found on the basis of pre-clinical tests that the cis-compound (code no. AF102B) was especially promising for the control of senile dementia of Alzheimer's type (SDAT). It is also of interest that each of the cis- and trans-isomers may be optically resolved, and the biological activity of the optical isomers was also investigated in a number of cases.

It is a principal object of the invention to provide novel 4- and 5- spiro-1,3-oxazoline and -1′,3-thiazoline compounds, which are distinctive from the aforementioned spirooxathiolane/quinuclidine compounds. Further objects of the invention, and especially those which relate to the provision of useful pharmaceutical compositions and methods for the treatment of disease, will be apparent from the description which follows.

SUMMARY OF INVENTION

The present invention provides novel compounds corresponding with the schematic structural formula (I):

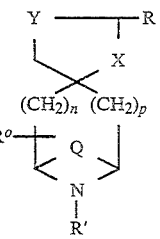

including enantiomers, racemates and acid addition and quaternary salts thereof, wherein Q is a member selected from two hydrogen atoms, $(CH_2)_m$ and $C(CH_3)_2$ where m is 1, 2 or 3 and n and p are each independently 0, 1, 2 or 3, provided that $n+p=1-3$, and $R^0$ is hydrogen, methyl or hydroxyl; the moiety

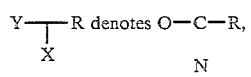

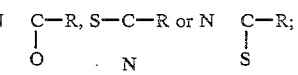

R is selected from hydrogen, $NH_2$, $NH—C_{1-6}$-alkyl, $N(C_{1-6}$-alkyl$)_2$, $C_{1-6}$-alkyl, $C_{2-6}$-alkenyl, $C_{2-6}$-alkynyl, $C_{3-7}$- cycloalkyl, $C_{1-6}$-alkyl substituted by 1–6 halogen atoms, hydroxy- $C_{1-6}$-alkyl, $C_{1-6}$-alkoxy, $C_{1-6}$-alkylthio, $C_{1-6}$-alkoxy-$C_{1-6}$-alkyl, carboxy-$C_{1-6}$-alkyl, ($C_{1-6}$-alkoxy)carbonyl-$C_{1-6}$-alkyl, amino-$C_{1-6}$-alkyl, mono($C_{1-6}$-alkyl)amino-$C_{1-6}$-alkyl, di-($C_{1-6}$-alkyl)amino-$C_{1-6}$-alkyl, 2-oxo-pyrrolidin-1-yl-methyl, aryl, diarylmethylol, and $C_{1-6}$-alkyl substituted by one or two aryl groups; R' is independently selected from the group from which R is selected and $C_{1-6}$-alkanoyl and arylcarbonyl; and aryl denotes unsubstituted phenyl or phenyl substituted by 1–3 substituents selected from halogen, $C_{1-6}$-alkyl, $C_{1-6}$-alkoxy and $CF_3$, subject to the provisos (i), (ii), (iii) and (iv), namely: (i) when Q is two hydrogen atoms, $n=p=1$, $R^0$ is hydrogen, R is $NH_2$ and R' is methyl, then the moiety

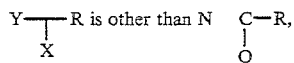

(ii) when Q is two hydrogen atoms, $n=p=1$, $R^0$ is hydrogen, and R is phenyl, then R' is not tertiary butyl, (iii) when Q is two hydrogen atoms, $n=p=1$, $R^0$ is hydrogen. R is p-chlorophenyl, and R' is tertiary butyl, then the moiety

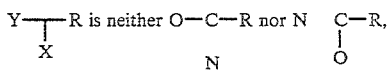

and (iv) when Q is two hydrogen atoms, $n=p=1$, $R^0$ is hydrogen, R is 3,5-dichlorophenyl, and R' is tertiary butyl, then the moiety

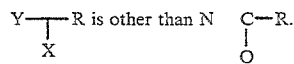

The present spiro compounds, in contrast to those mentioned above, may exhibit optical isomerism, and only in a few cases geometrical isomerism. Optical isomerism will be shown in particular, when R and/or R' is asymmetrical, and/or the spiro-ring containing only a single nitrogen as ring hetero-atom is asymmetrical with respect to the spiro-junction.

The compounds of formula (I) as defined above are new. The compound of formula (I) in which Q is two hydrogen atoms, n=p=1, $R^0$ is hydrogen, R is $NH_2$ and R' is methyl, and the moiety

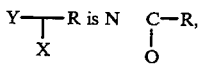

was one of a series of compounds tested by Harnden and Rasmussen (J. Med. Chem. 1970, 23: 305–308) for CNS stimulant activity, but was not one of the five compounds selected as being the most active of the series. The compounds of formula (I) in which Q is two hydrogen atoms, n=p=1, $R^0$ is hydrogen, R is phenyl, and R' is tertiary butyl, are known, as are those in which Q, n, p, $R^0$ and R' have these values and either R is p-chlorophenyl, while the moiety

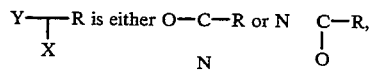

or R is 3,5-dichlorophenyl, while the moiety

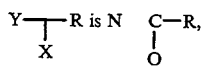

are known (see Jones et al, J. Chem. Soc. (B) 1308–1315, 1971), but no biological activity was reported in respect of these compounds.

It will be appreciated that in the pharmaceutical compositions and the methods of treatment in accordance with the present invention, the above-stated provisos (ii), (iii) and (iv) do not apply.

European Patent Application No. 0337547A1, published Oct. 18, 1989, discloses compounds said to be useful in the treatment of psychotic disorders, presenile and senile dementia, and other physiological conditions, of the following formula:

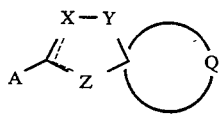

in which the broken line represents an optional bond in one of the two positions, A represents a group of formula

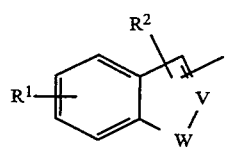

(in which $R^1$ and $R^2$ are independently hydrogen or specified substituents, V is N, —CH or —C—, and W is O, S, or NH which may be substituted by specified substituents), Q is the residue of an azacyclic or azabicyclic system, and of X, Y and Z, two are selected independently from O, S and N and the other is C, or Y may be C=O. This reference does not detail results of any biological testing, but states that certain of the disclosed compounds (not specified) demonstrate an affinity for the 5-$HT_3$ receptors. This reference gives no directions based on biological activity for selecting any particular one of the numerous possible structures represented by permutations of the moieties represented by the symbols Q, X, Y and Z depicted above, in combination with the essential bicyclic radical A.

In the compounds of formula (I), examples of the ring joined in spiro manner to the oxazoline or thiazoline ring in formula (I) are, when Q is two hydrogen atoms, pyrrolidine, piperidine and hexamethyleneimine; and when Q is other than two hydrogen atoms, examples are: 5-azabicyclo[2,1,1]hexane, 6,6,-dimethyl-5-azabicyclo[2,1,1]hexane, 7-azabicyclo[2,2,1]heptane, 8-azabicyclo[3,2,1]octane, 6-azabicyclo[3,1,1]heptane, 7,7,-dimethyl-6-azabicyclo[3,1,1]8-azabicyclo[3,2,1]octane, 9-azabicyclo[3,3,1]nonane, 7-azabicyclo[4,1,1]octane, 8,8,-dimethyl -7-azabicyclo[4,1,1]octane, 9-azabicyclo[4,2,1]nonane, and 10-azabicyclo[4,3,1]decane. Moreover, as indicated by the symbol $R^0$ in formula (I), any of these ring systems may be ring-substituted by methyl or OH.

The spiro-compounds provided by the present invention have central and peripheral nervous system activity.

In a presently preferred group of compounds, R may be hydrogen, NH-$C_{1-6}$-alkyl. N($C_{1-6}$-alkyl)$_2$, $C_{1-6}$-alkyl or aryl, while R' may be hydrogen or methyl. Without prejudice to the generality of the invention, exemplary of the present compounds are: 1-methylpiperidine-4-spiro-4'-(2'-methyl-1',3'-oxazoline), 1-methylpiperidine-4-spiro-4'-(2'-ethyl-1',3'-oxazoline), 2-methylspiro(1,3-oxazoline-5,4')-1'-methylpiperidine, 2-methylspiro(1,3-thiazoline-5,4')-1'-methylpiperidine, 2-ethylspiro(1,3-oxazoline-5,4')-1'-methylpiperidine, including the acid addition and quaternary salts thereof.

The present invention moreover provides pharmaceutical compositions for use in treating diseases of the central and peripheral nervous system in mammals, which comprise an amount effective for use in treating these diseases, of at least one of the spiro-compounds of the invention. Further, the invention provides methods for treating diseases of the central and peripheral nervous system in mammals, which comprise administering to a mammal an amount effective for use in treating these diseases, of at least one of the spiro-compounds of the invention. As indicated above, provisos (ii), (ii) and (iv) do not apply to such compositions and methods.

DETAILED DESCRIPTION OF THE INVENTION

The above spiro-compounds of formula (I), may be prepared by reacting suitably substituted compounds containing the saturated nitrogen-only ring system with a reactant which will effect formation of the oxazoline ring. Thus, for example, a suitable starting material is 4-aminomethyl-1-methylpiperidin4-ol, which may be prepared either from 4-nitromethyl-1-methylpiperidin-4-ol e.g. as the HCl salt, as in Scheme A, or from 4-azidomethyl-1-methylpiperidin-4-ol as in Scheme B.

Scheme A

-continued

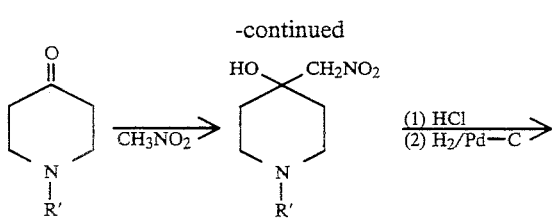

Scheme B

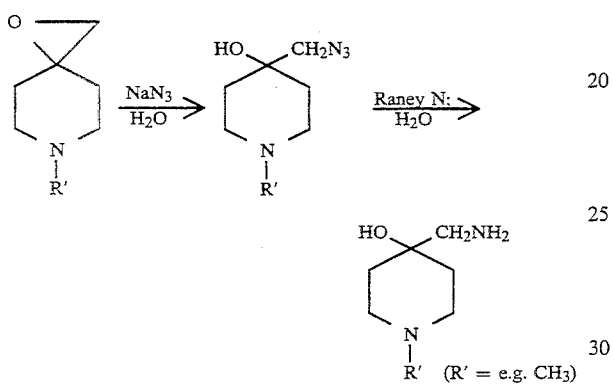

It should be noted that in Scheme B, reaction of sodium azide with the epoxide of 4-methylene-1-methylpiperidine in aqueous solution results in formation of a single product, 4-azidomethyl-1-methylpiperidin-4-ol, while addition to the latter of wet active Raney Nickel until the evolution of nitrogen ceases results in the formation of the desired compound. The major advantages of the Scheme B approach are:

a) there is no need to isolate any intermediates; and
b) no hydrogenation apparatus is needed since the hydrogen content of the catalyst is sufficient.

It has now surprisingly been found that the 3-aminomethyl product of either of these reaction schemes may be readily condensed with a carboxylic acid RCOOH to give the spiro-products, whereas it was previously believed that formation of the oxazoline ring by condensation of amino-alcohol and carboxylic acid would proceed smoothly only when the amino-alcohol is completely substituted on the carbon atom to which the NH$_2$ group is connected [see "Oxazolines, their Preparation, Reactions and Applications", J. A. Frunp, Chem. Rev. 71,483–505 (1971)]. The corresponding imidate RC(:NH)—O-alkyl can be alternatively used, in place of the carboxylic acid RCOOH. The reactions affording compounds of formula I may be illustrated (e.g. in the case of spiro oxazoline/piperidines) as follows:

Scheme C

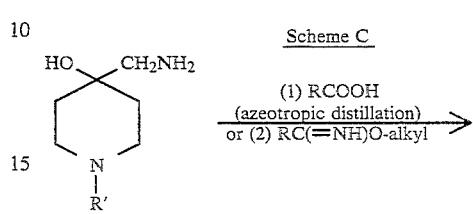

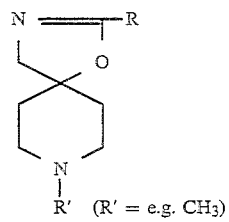

In order to obtain the spiro-compounds when R=NH$_2$, however, it is preferred to react cyanogen bromide with, for example, 4-aminomethyl-1-methyl-piperidin-4-ol.

It will be appreciated that while the foregoing methods will be effective to prepare those compounds of the invention in which

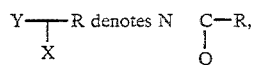

in order to apply similar methods for the purpose of preparing compounds of the invention in which

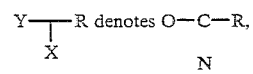

a suitable starting material would be (illustratively, where the ring spiro-connected to oxazoline is piperidine) 4-amino-4-hydroxymethyl-1-methylpiperidine. This starting material and the final product may be prepared, e.g., according to Scheme D or E:

Scheme D

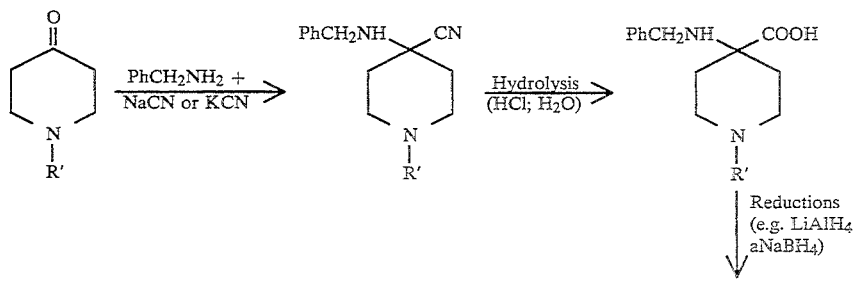

Scheme D

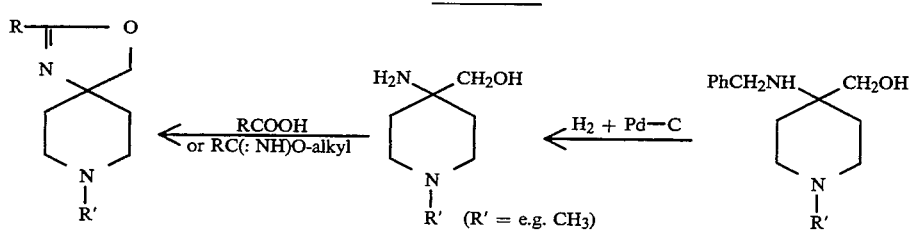

Scheme E

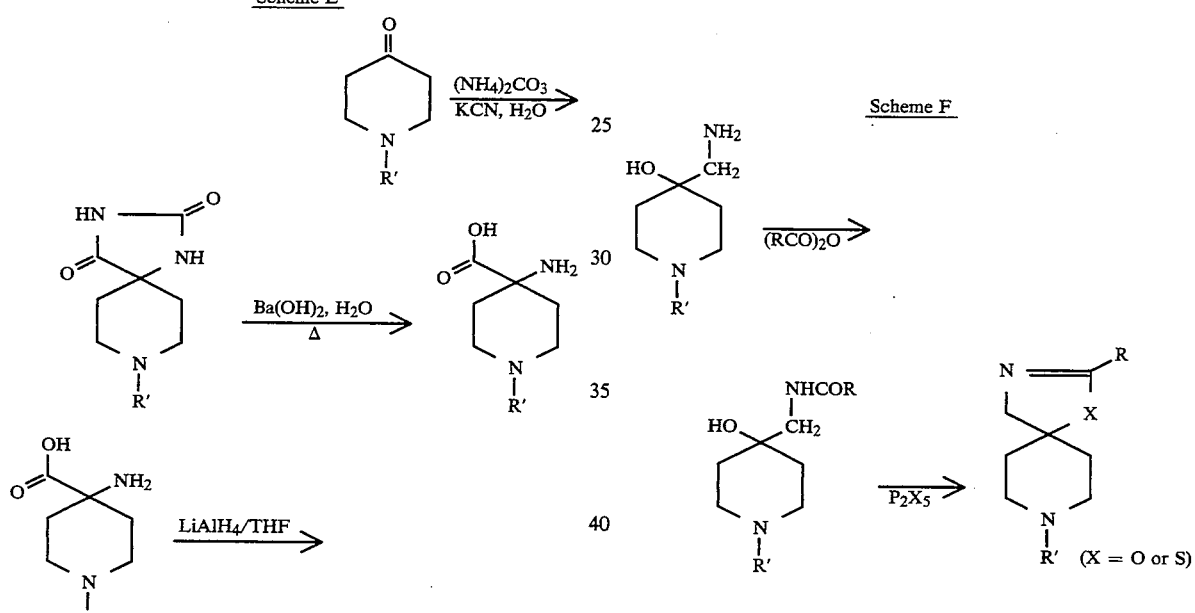

Scheme F

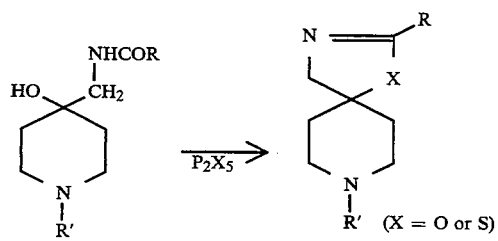

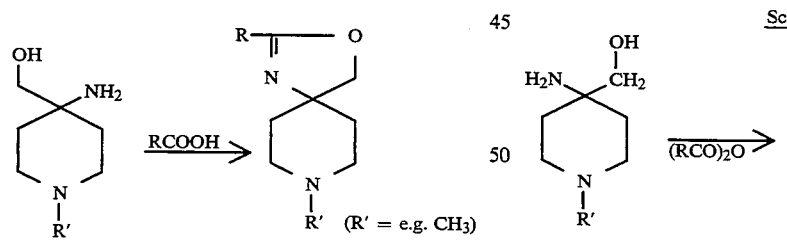

It may be noted that in those cases where the spirocompounds of the invention exhibit optical activity, the racemates can be resolved by use of optically active acids such as dibenzoyl-L- or D-tartaric acid, ditolyl-L- or D-tartaric acid.

When $$Y\!\!-\!\!\!\underset{X}{\overset{\phantom{|}}{\top}}\!\!-\!\!R \text{ denotes N}\!\!-\!\!\!\underset{S}{\overset{C-R}{|}}\!\!\text{ or } S\!\!-\!\!\underset{N}{\overset{C-R,}{|}}$$

these compounds can be prepared by the following Schemes F and G, e.g., when the ring spiro connected to thiazoline is piperidine.

Scheme G

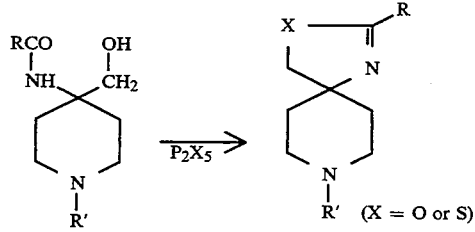

Additional methods include preparation of the corresponding epoxide or thioepoxide and reacting it with an appropriate nitrile, as in Scheme H, where the ring spiro connected to the oxazoline or thiazoline ring is e.g., piperidine.

Scheme H

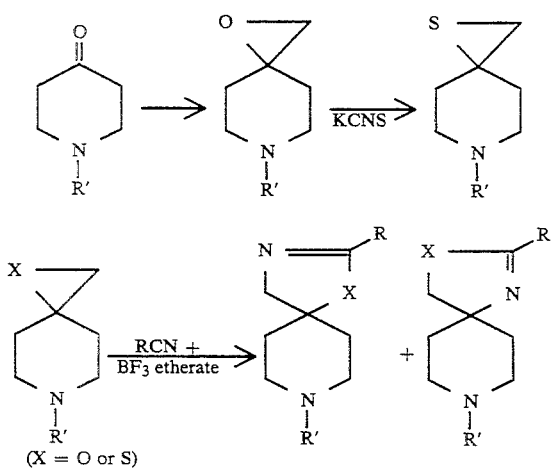

(X = O or S)

The compounds of formula (I), whether forming per se an embodiment of the invention, or contained in the pharmaceutical compositions of the invention, or utilized in the methods of the invention, include addition and quaternary salts of these compounds. By way of example, acid addition salts for pharmaceutical use include those formed from such acids as hydrochloric, hydrobromic, rumuric, maleic, oxalic, malonic, malic, acetic, citric, tartaric, dibenzoyl D- and L-tartaric, ditoluoyl D- and L-tartaric, salicylic, carbonic, aspartic and glutamic acids.

At least those spiro-compounds of the present invention where R is methyl are centrally active muscarinic agonists. Due to their pharmacological properties, these compounds can activate central cholinergic functions under conditions where the cholinergic system is hypofunctional.

The spiro-compounds of the invention are in general potentially useful for the treatment of presenile and senile dementia, senile dementia of Alzheimer's type (SDAT), atypical Alzheimer's disease (Perry et al, Advances in Neurology, eds. R. J. Wurtman et al., 51:41, 1990), combined multiinfract dementia and Alzheimer's disease, age-associated memory impairments (AAMI), acute confusion disorders, emotional and attention disorders, mania, tardive-dyskinesia, hyperkinesia, mixed Alzheimer's and Parkinson's disease, aphasia, hallucinatory-states, post encephalitic amnesic syndrome, alcohol withdrawal symptoms, Huntington's chorea, Pick's disease, Friedrick's ataxia, Gilles de la Tourette disease and Down syndrome, because all of these disease states are disturbances in which a central cholinergic hypofunction has been implicated at least to a certain extent. The spiro-compounds of this invention are also potentially analgesic agents and therefore may be useful in the treatment of severe painful conditions such as rheumatism, arthritis and terminal illness. The spiro-compounds of the invention in which R is methyl, would appear to be of particular potential value for the treatment of SDAT and related disorders.

The spiro-compounds of the present invention may be used in combination with acetyl cholinesterase inhibitors such as physostigmine or tetrahydroaminoacridine; in combination with acetylcholine precursors such as choline or lecithin; in addition to "nootropic" drugs such as piracetam, aniracetam, oxiracetam, or pramiracetam; in addition to compounds that interact with $Ca^{2+}$ channels such as 4-aminopyridine or 3,4-diaminopyridine; or in addition to peptides that can have modulatory effects on acetylcholine release, such as somatostatin; in combination with a peripheral antimuscarinic agent (such as pirenzepine, N-methylatropine, N-butylscopolamine, propantheline, methantheline, glycopyrrolate, or tropenzilium) to counteract peripheral adverse effects that might be expected at high doses, such as salivation, diarrhea, gastric secretion or vomiting, or in combination with transdermal scopolamine such as Scopoderm ® to counteract nausea and/or vomiting; in combination with antidepressants such as nortriptyline, amitriptyline, imipramine, minaprine in order to alleviate both the cognitive impairments and depressive symptoms associated sometimes with SDAT, AAMI, mixed SDAT/Parkinson's disease (PD); in combination with M2-antimuscarinic drugs such as secoverine, AFDX-116(c.f. Hammer et al, Life Sci. 38: 1653, 1986) in order to counteract peripheral adverse side effects that might be expected at high doses of the compounds, to counteract inhibitory effects of such agonists at central inhibitory presynaptic and postsynaptic receptors of M2 type and to potentiate the release of acetylcholine via inhibition of inhibitory autoreceptors of M2 type at intact terminals; in combination with nicotinic agonists such as nicotine in order to stimulate both the nicotinic and muscarinic receptors in the brain; in combination with an adrenergic agonist (clonidine or quanfamicine) in order to alleviate both the cognitive and other impairments associated with a mixed cholinergic-noradrenergic deficiency in SDAT; in combination with inhibitors of neuronal serotonin reuptake such as alaproclate, zimelidine in order to alleviate both the cognitive and other emotional functions in SDAT; in combination with monoamine oxidase-B inhibitors like deprenyl in order to alleviate both cognitive and other motor impairments associated with mixed states such as SDAT/PD; in combination with Nerve Growth Factor (NGF, which is administered either by a nasal spray or intracerebroventricularly).

The spiro-compounds of the present invention, with or without the aforementioned other active substances, can be administered for example, by way of injection in a suitable diluent or carrier, per os, rectally in the form of suppositories, by way of insufflation or nasal spray, by infusion or transdermally in a suitable vehicle with or without physostigmine or tetrahydroaminoacridine, for example by using the device which is the subject of U.S. Pat. No. 2,163,347 (issued Nov. 29, 1988).

The present spiro-compounds, especially where methyl, are also of potential use For the treatment of disorders requiring the application of a long-lasting cholinergic agent of mild local activity. Such an agent is needed in disorders such as glaucoma, as the compound is not destroyed by the enzyme which deactivates acetylcholine, i.e. acetyl- and butyryl-cholinesterase, and may also be used for the treatment of peripheral cholinergic disorders such as myasthenia gravis, urinary bladder dysfunctions, Adi's disease and Eaton-Lambert disease. These compounds might also be used in disturbances where cholinergic underactivity is induced by drugs.

It appears that the present spiro-compounds, especially where R is $C_{3-6}$-alkyl or aryl, are anticholinergic agents and may potentially be used for treatment of disorders due to a cholinergic hyperfunction, whether this be spontaneous or drug-induced. These compounds are of potential use in the treatment of various diseases such as PD, pseudo-PD, mixed AD/PD, primary dystonias, spasmodic torticollis, cranial dystonia, depression, motion sickness, akathisia (after neuroleptic withdrawal), central hypertension, human head injury, mixed tardive dyskinesia and PD, manic-depression, as adjuncts in surgery instead of atropine, scopolamine, etc., in intoxication due to an excess of acetylcholine like inhibition of acetylcholinesterase. These may also be used in ophthalmology when either prolonged or short-term mydriasis is required.

The present spiro-compounds may also potentially be used in the treatment of disease characterized by excess peripheral-like activity such as asthma, chronic obstructive pulmonary disease, peptic ulcer disease. For these peripheral disorders it is recommended to use the quaternary salts of the formula (Ia)

compounds, where the tertiary nitrogen is quaternized by R″, where this is, for example, lower ($C_{1-6}$) alkyl, aryl such as phenyl, or aryl-substituted $C_{1-6}$ alkyl such as benzyl.

The invention will now be illustrated by the following non-limiting Examples.

EXAMPLE I

2-Methyl-spiro(1,3-oxazoline-5,4′)-1′-methylpiperidine
(I; R=R′=methyl - "AF150")

(a) 1-Methyl-4-nitromethylpiperidin-4-ol hydrochloride

This starting material was prepared using a slight modification of the method of A. D. Cale (U.S. Pat. No. 4,746,655, 1988). A mixture of N-methylpiperidinone (142 g., 1.28 mole) and nitromethane (78.1 g., 1.28 mole), was added to a well-stirred solution of sodium ethoxide (1.28 mole), 20% in ethanol, maintaining the internal temperature at 5°–8° C. A white solid precipitates, the stirring is continued for 20 minutes and another 40 minutes at room temperature. The resulting solution was acidified with 500 ml. of 7.2N HCl in isopropyl alcohol. The hydrochloride and the inorganic salts were extracted with $CH_3OH$ (3×200 ml) and the solvent removed in vacuo to give the title compound, m.p. 180°–182° C. (non hygroscopic).

m/z: 174 (M+ of free base, 100%), 157 (M—OH, 20%), 127 (M—H—$NO_2$, 25%), 113 (M—$NO_2$—$CH_3$, 40%).

(b) 4-Aminomethyl-1-methylpiperidin-4-ol hydrochloride

Palladium on charcoal (10%, 4 g.) was added portionwise to a solution of 1-methyl-4-nitromethylpiperidin-4-ol (133.5 g.) in methanol (1500 ml). The compound was hydrogenated in a Paar at a pressure of 55 psi at room temperature for 48 hours. The solution was cautiously filtered, treated with active charcoal, the solvent removed and the residue was triturated with ethanol (200 ml.) to give the title compound, m.p. 177°–179° C.

m/z: 144(M+ of free base, 15%), 127 (M—OH, 25%), 114 (M—$CH_2NH_2$, 100%).

(c) 2-Methyl-spiro(1,3-oxazoline 5,4′)-1′-methylpiperidine (AF150)

A solution of KOH (1.43 g. of 86%) in methanol (50 ml.) was added to a solution of 4-aminomethyl-1-methylpiperidin-4-ol hydrochloride (3.61 g., 0.02 mole) in absolute methanol (50 ml.). After stirring for 10 minutes, a solution of ethyl acetimidate hydrochloride (2.7 g.) in 20 ml. absolute methanol was added, and stirring continued for 30 minutes at room temperature. The solvent was removed, and the residual solid was dissolved in a solution of 2.8 g. $Na_2CO_3$ in 50 ml. water, which was concentrated to dryness in vacuo. The white solid, was extracted with 2×50 ml. chloroform, treated with active charcoal, dried ($NB_2SO_4$) and the solvent removed to afford the title product (62.5% yield), m.p. 45° C. (sublimed at 40° C./0.05 mm Hg), giving a single spot on silica TLC eluted with 2% $NH_3$ in $CH_3OH$, Rf=0.4.

m/z: 168 (M+ of free base, 100% at 7.5 ev).

$^1$H-NMR (300 MHz, $CDCl_3$): δ 3.56 (2H, q, J=1.5 Hz), 2.53 (4H, m), 2.34 (3H, s), 1.96 (3H, t, J=1.5 Hz), 1.82 (4H, m).

Replacement of the KOH used in this Example by the equivalent amount of NaOH or $Et_3N$, gave similar results.

(d) 2-Methyl-spiro(1,3-oxazoline 5,4′)-1′-methylpiperidine Dibenzoyl-D-tartrate

A hot solution of dibenzoyl-D-tartaric acid (5.4 g., 15 mmole) in 500 ml. toluene was added while stirring to AF150 (5.5 g., 32 mmole) dissolved in 200 ml. dry toluene. The precipitate was allowed to settle and the supernatant liquid was decanted off. The residual solid was washed with 3×100 ml. dry toluene and dried under reduced pressure to afford 8.4 g. (80% yield) of a white slightly hygroscopic solid.

TLC chloroform/alumina (Merck Art 5581) Rf=0.4.
m/z: 168 (M+)

$^1$H-NMR (300 MHz, $D_2O$ containing 1.5 mg. $Na_2CO_3$/0.5 ml. $D_2O$): δ1.95 (s, 6H, $CH_3$—C), 2.35 (s, 6H, $CH_3$—N), 3.5 (s, 4H, $CH_2$), 5.7 (s, 2H), 7.5–8.2 (m, 10H, aromatic hydrogens).

EXAMPLE II

2-Ethyl-spiro(1,3-oxazoline-5,4′) -1′-methylpiperidine
(I; R=ethyl, R′=methyl)

This compound was prepared similarly to the compound of Example I, using the equivalent amount of ethyl propionimidate hydrochloride, in place of ethyl acetimidate hydrochloride. The product was obtained as a liquid, b.p. 53°/0.03 mm Hg, in 60.5% yield.

$^1$H-NMR (300 MHz, $CDCl_3$): δ 3.52 (2H, t, J=1.5 Hz), 2.47 (4H, m), 2.30 (3H, s), 2.26 [2H, quartet (J=Hz), triplets (J=1.5 Hz)], 1.86 (2H, m), 1.72 (2H, m), 1.18 (3H, t).

EXAMPLE III

1-Methylpiperidine-4-spiro-4′-(2′-methyl-1′,3′-oxazoline
(I; R=R′=methyl - "AF151")

(a) 1-Methylpiperidine-4-spiro-5′-hydantoin

A mixture of solutions of 1-methylpiperidine-4-one (36.44 g., 0.322 mole) in ethanol (150 ml.), ammonium carbonate (93.0 g., 0.968 mole) in water (400 ml.) and potassium cyanide (25.8 g., 0.396 mole) in water (82 ml.), was heated at 60° C. for 2.5 hours and then left at room temperature overnight, when 1-methylpiperidine- 4-spiro-5'-hydantoin separated. It was filtered off and washed with small amounts of cold water, ethanol and ether, to give a crystalline powder (27.0 g.). Concentration of the filtrate and washings gave a second crop (20.0 g.). The product was crystallized from methanol: m.p. 265°-276° (dec.).

IR (KBr) 3170 (NH); 1700 (C=O) cm$^{-1}$
m/z 183(M$^+$, 38%); 71 (100%)
$^1$H-NMR (300 MHz, D$_2$O): δ 1.8 (2H), 2.06 (sextet, 2H), 2.49 (S, —CH$_3$), 2.58 (t, 2H), 3.14 (t, 1H), 3.20 (t, 1H).

(b) 4-Amino-1-methylpiperidine-4-carboxylic acid 1-methylpiperidine-4-spiro-5'-hydantoin (9.75 g., 0.0533 mole) and barium hydroxide octahydrate (28.8 g., 0.00913 mole) in water (150 ml.) were heated at 160° C. in an autoclave for three hours. The contents of four such batches were combined and the precipitated barium carbonate was filtered off. The filtrate was neutralized with solid carbon dioxide and the precipitate was removed by filtration. The filtrate was concentrated to a small volume to give 4-amino-1-methylpiperidine-4-carboxylic acid (32.0 g., 95% yield), m.p. 275°-280° C. (dec.).

IR (KBr) 3300, 1655, 1580 cm$^{-1}$
m/z 158(M$^+$, 90%); 141 (98%, M—OH); 113 (12%, M—CO$_2$H); 96 (100%); 71 (52%)
$^1$H-NMR (300 MHz, C$_5$D$_5$N+D$_2$O): δ 1.2 (m, 2H), 1.48 (s, CH$_3$N—), 1.7 (m, 2H), 1.9 (m, 2H), 2.0 (m, 2H).

(c) 4-Amino-4-hydroxymethyl-1-methylperidine

Lithium aluminum hydride powder (15.62 g., 0.412 mole) in dry tetrahydrofuran (THF) (600 ml.) was heated under reflux for 15 minutes, after which 4-amino-1-methylpiperidine-4-carboxylic acid (31.0 g., 0.196 mole) in the form of a dry powder was added portionwise under nitrogen, with efficient stirring. After the addition was completed, the reaction mixture was heated under reflux for four hours, cooled to 0° C. under nitrogen with efficient stirring, worked up by careful slow addition of water (20 ml.), 15% aqueous NaOH (20 ml.) and again water (10 ml.). The reaction mixture was filtered and the precipitate was extracted with boiling THF (3×150 ml.). The THP filtrate and the extracts were combined and the solvent removed at 25 mm to give a yellow viscous oil (28.0 g., 98.9% yield).

IR (neat) 3320 (NH), 3200 (br. OH), 1587 (NH$_2$), 1468, 1448 cm$^{-1}$
m/z 144(M$^+$, 15%); 127 (M—OH); 113 (M—CO$_2$H); 96 (100%); 70 (41%).
$^1$H-NMR (300 MHz, CDCl$_3$): δ 1.41 (m, 2H), 1.60 (m, 2H), 2.24 (s, CH$_3$—N), 2.29 (m, 2H), 2.48 (m, 2H), 2.50 (br., —NH$_2$), 3.29 (s, —CH$_2$OH).

(d) 1-methylpiperidine-4-spiro-4'-(2'-methyl-1',3'-oxazoline) (AF151)

A mixture of 4-amino-4-hydroxymethyl-1-methylpiperidine (1.80 g.) with acetic acid (20 ml.) and xylene (20 ml.) was azeotropically distilled for 28 hours. The remaining acetic acid and xylene were removed at reduced pressure (25 mm Hg) to leave a residual viscous oil which was basilled to pH 11 with an aqueous solution of K$_2$CO$_3$. Extraction with chloroform and evaporation of the extract gave a small amount of residual brown oil (0.27 g.). The aqueous solution remaining after chloroform extraction was evaporated to remove water, the residual solid was extracted with chloroform and the extract was dried (Na$_2$SO$_4$) and evaporated, to afford as residue a very hygroscopic solid (3.0 g.). TLC showed that the latter gave mainly one spot, which was more polar than the starting amino-alcohol.

A portion of the hygroscopic solid, which melted at 150°-160° C., was heated under vacuum, and almost immediately began to distil as a colorless oil at 45° C./0.15 mm Hg. This oil, on keeping in the freezer, formed crystalline needles melting at room temperature. The distillate was the acetic acid salt of the title compound.

IR (neat) 1664 (—C=N); 1565 & 1398 (—CO$_2$—); 1256 (C—O) cm$^{-1}$
m/z 168(M$^+$ of free base); 109; 70.
$^1$H-NMR (300 MHz, CDCl$_3$): δ 1.77 (m, 2H), 1.96 (m, 2H), 1.98 (s, CH$_3$—), 2.0 (s, CH$_3$—), 2.49 (s, CH$_3$—N—), 2.91 (m, 4H), 3.95 (s, —CH$_2$O—), 9.30 (br. s, —CO$_2$H).
$^{13}$C-NMR (300 MHz, CDCl$_3$): δ 14.0 (CH$_3$CO$_2$—), 22.9 (CH$_3$C=N—), 35.6 (C$_3$ and C$_5$), 44.4 (CH$_3$N$^+$), 51.1 (C$_2$ and C$_6$), 67.0 (C$_4$), 77.4 (C$_{5'}$), 164.3 (C—=N), 176.7 (—CO$_2$—).
$^1$H-NMR of free base (300 MHz, CDCl$_3$): δ 1.64 (m, 2H), 1.84 (m, 2H), 1.98 (s, CH$_3$—), 2.26 (m, 2H), 2.30 (s, CH$_3$—), 2.69 (m, 2H), 3.94 (s, —CH$_2$—).

EXAMPLE IV

1-Methylpiperidine-4-spiro-4'-(2'-ethyl-1',3'-oxazoline)

A mixture of 4-amino-4-hydroxymethyl-1-methylpiperidine (3.0 g.) with propionic acid (50 ml.) and xylene (90 ml.) was azeotropically distilled for 5 hours. The residue (7 ml.) was basified to pH 11-12 with an aqueous solution of K$_2$CO$_3$. Extraction with chloroform and evaporation of the extract gave a mixture of non-polar compounds (0.80 g.). The aqueous solution remaining after chloroform extraction was evaporated to remove water, the residual solid was extracted with chloroform and the extract was dried (Na$_2$SO$_4$) and evaporated, to afford as residue a hygroscopic solid (3.6 g.). TLC showed that the latter gave mainly one spot, which was more polar than the starting amino-alcohol (silica gel, solvent 40:58:2 methanol-chloroform-aqueous ammonia).

A portion of the hygroscopic solid (1.5 g.) was heated under vacuum, and almost immediately began to distil as a viscous colorless oil at 50° C./0.1 mm Hg. The distillate is the propionic acid salt of the title compound.

m/z 182(M$^+$ of free base, 14%); 167 (5%), 154 (71%), 125 (9%), 109 (100%), 96 (45%), 81 (30%), 74 (57%), 70 (89%), 57 (64%).
$^1$H-NMR (300 MHz, CDCl$_3$): δ 1.12 (t, J=7.5 Hz, CHCH$_2$—), 1.17 (t, J=7.6 Hz, CH$_3$CH$_2$—), 1.75 (m, 2H), 2.00 (m, 2H), 2.29 (q, J=7.5, CH$_3$CH$_2$—), 2.30 (q, J=7.6, CH$_3$CH$_2$—), 2.56 (s, CH$_3$N—), 3.02 (m, 2—CH$_2$—), 3.95 (s, —CH$_2$O—), 7.52 (hr. —CO$_2$H).

To a stirred solution of the above propionic acid salt (700 mg.) in chloroform, a saturated aqueous solution of K$_2$CO$_3$ was added until evolution of CO$_2$ had ceased. The mixture was then stirred for 0.5 hour and the phases were separated. The aqueous phase was extracted with chloroform, the combined separated chloroform phase and the extracts were dried (Na$_2$SO$_4$), and the solvent was evaporated to afford the title compound in free base form as a residual colorless oil (550 mg.), which showed a single spot on TLC.

$^1$H-NMR (300 MHz, CDCl$_3$): δ 1.17 (t, J=7.6 Hz, CH$_3$CH$_2$—), 1.61 (m, —CH$_2$—), 1.86 (m, —CH$_2$—), 2.18 (m, —CH$_2$—), 2.29 (q, J=7.6, CH$_3$CH$_2$—), 2.30 (s, CH$_3$N—), 2.71 (m, —CH$_2$—), 3.94 (s, —CH$_2$O—).

m/z 182(M+ 25%), 167 (9%). 154 (78%), 125 (17%), 109 (100%), 96 (65%), 81 (54%), 70 (96%), 57 (77%).

An alternative route to compounds such as AF150 and AF151 depends on the cyclodehydration of the appropriate amides, as shown in the following illustrations:

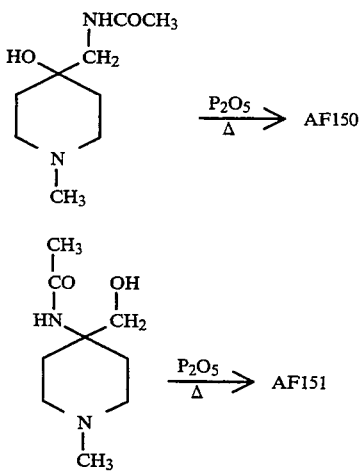

Dehydrating agents such as $P_2O_5$, sulfuric acid, $BF_3$-etherate, $CaCl_2$, and molecular sieves, can be used for the above reactions. Corresponding thiazolines instead of oxazolines can be obtained by analogous reactions using $P_2S_5$.

EXAMPLE V

2-Methyl-spiro(1,3-thiazoline-5,4')-N-methylpiperidine (I; R=R'=methyl - "AF150(S)")

(a) 4-Acetamidomethyl-4-hydroxy-1-methylpiperidine

4-Aminomethyl-4-hydroxy-1-methylpiperidine (0.83 g., 5.7 mmole) was dissolved in 10 ml. chloroform, and acetic anhydride (0.58 g., 5.7 mmole) was added. The reaction mixture warmed spontaneously to 40°–50° C. After 30 minutes, the solvent was evaporated and the crude residue was chromatographed on a silica gel column (Merck 7734), using 33:67 2% aqueous ammonia-methanol as eluent.

m/z 186 (M+)

$^1$H-NMR (300 MHz, CDCl$_3$): δ 1.60 (multiplet, 4H, H3 and H4), 2.01 (singlet, 3H, CH$_3$—C), 2.29 (singlet, 3H, CH$_3$—N), 2.38 (multiplet, 2H, H1), 2.55 (multiplet, 2H, H2), 2.98 (multiplet, 1H, NH), 3.26 (doublet, 2H, H5) ppm.

$^1$H-NMR (300 MHz, D$_2$O): δ 1.42 (multiplet, 4H, H3 and H4), 1.81 (singlet, 3H, CH$_3$—C), 2.08 (singlet, 3H, CH$_3$—N), 2.27 (multiplet, 2H, H1), 2.46 (multiplet, 2H, H2), 3.03 (singlet, 2H, H) ppm.

The impurity gives a peak at 3.44 ppm.

(b) 2-Methyl-spiro(1,3-thiazoline 5,4)-N-methylpiperidine

A mixture of 4-acetamidomethyl-4-hydroxy-1-methylpiperidine (6.5 g., 35 mmole) with phosphorus pentasulfide (10 g., 22 mole) was heated at 220° C. for 30 minutes, cooled, and dissolved in 30 ml. concentrated hydrochloric acid. The acidic solution was transferred to 100 ml. cold concentrated aqueous sodium hydroxide, extracted with 2×100 ml. chloroform, and the combined extracts were dried and evaporated to afford 5 g. of a black oily residue, which was purified by distillation at 75° C./1 mm Hg to yield 1.8 g. clear liquid.

m/z: 184 (M+)

$^1$H-NMR (300 MHz, CDCl$_3$): δ 1.8–2.0 (m, 4H), 2.17 (t, 3H, CH$_3$—C), 2.2 (s, 3H, CH$_3$—N), 3.9 (q, 2H, CH$_2$-thiazoline ring).

BIOLOGICAL TESTING

The compounds according to the invention, exhibit pharmacological activity and are therefore useful as pharmaceuticals, e.g. for therapy. In particular the agonists show activity in the tests detailed below. In the Tables which report the results of such tests, certain compounds may be denoted by the following reference numerals:

| | | |
|---|---|---|
| (1) Carbachol | (5) AF150 ■ | (9) McN-A-343 |
| (2) Oxotremorine-M | (6) AF151 ■ | (10) Pirenzepine |
| (3) Oxotremorine | (7) AF150(S) ■ | (11) Atropine |
| (4) AF102B* | (8) AF125 ♦ | (12) Scopolamine |

*cis-2-methylspiro(1,3-oxathiolane-5',3)quinuclidine (U.S. Pat. No. 4,855,290)
■ exemplified compounds of the present invention
♦ 2-methylspiro(1,3-oxazoline-5',3)quinuclidine
(U.S.S.N. 07/507,228 filed April 10, 1990)

TEST 1

Isolated Guinea-Pig Ileum Preparation

The compound of Example I (AF150) is a full muscarinic agonist—having an EC$_{50}$=0.8 μM (blocked by atropine 10 μM). When compared to acetylcholine (ACh), AF150 is capable of inducing a maximal contraction of the ileum of 130% (ACh=100%). Surprisingly, the shape of the curve of AF150 as compared with ACh is different and this curve can be analyzed by a two- or even a three-sites model. This can indicate that AF150 has different affinities to the subtypes of muscarinic receptors found in this preparation. Moreover, the compound of Example III (AF151) is also a full muscarinic agonist—having an EC$_{50}$=3 μM (blocked by atropine 10 μM).

TEST 2

Binding to Muscarinic Receptors in the Brain

The binding of agonists to M1 muscarinic receptors and the effect of guanylyl imidophosphate (GppNHp). Agonists are known to be coupled with guanine nucleotide binding proteins (G proteins). While numerous studies of agonist binding to the M2 muscarinic receptor (low-affinity pirenzepine) have been done, relatively few studies have examined agonist binding to M1 muscarinic (high-affinity pirenzepine) receptors. The primary reason appears to be that most agonists (except AF102B for example, U.S. Pat. No. 4,855,290) have a higher affinity for the M2-subtype than for M1 muscarinic receptors.

Non-hydrolyzable guanine nucleotides such as GppNHp dissociate the G protein from the receptor and decrease the affinity of the receptor for agonists but not for antagonists. Under special conditions it is possible to analyze both the affinity as well as the efficacy of agonist with M1 muscarinic receptors using low concentrations of $^3$H-pirenzepine ($^3$H-PZ) bellow its K$_D$ [Potter et al, Cell. Molec. Neurobiol 8:181–191 (1988); Potter and Ferrendelli, J. Pharmacol. Exp. Ther. 248: 974–978 (1989); Flynn et al, Eur. J. Pharmacol. 172:363–372 (1989)].

Under these conditions agonists of high efficacy ("full agonists") bind directly to the M1 receptor subtype with two affinities. The higher affinity state of the M1 receptor subtype is sensitive to guanine nucleotides and GppNHp, for example, converts the high-affinity state to a low-affinity state. The ratio of low and high affinities ($K_L/K_H$) of the M1 receptor may predict the relative efficacies of agonists to activate putative M1 receptor-mediated second messenger systems.

Table 1 summarizes the results obtained oxotremorine-M and carbachol (two full but non-selective M1 and M2 agonists), for the selective M1 agonist AF102B (U.S. Pat. No. 4,855,290), AF150 and AF151. As expected, the quaternary full agonists, oxotremorine-M and carbachol show a two-affinity state and the relative efficacy of these compounds is predicted by the ratio of $K_L/K_H$. On the other hand, AF102B shows a mass-action curve.

may be particularly suited for the treatment of disorders with cholinergic hypofunction such as SDAT.

TEST 3

The two-affinity state of AF150 is preserved from homogenates of rat cerebral cortex also when the displacement of $^3$H-PZ is performed in a 10 mM sodium-potassium buffer indicating that this is a unique agonist when compared with other putative muscarinic agonists (Table 2). AF150 shows an excellent selectivity and efficacy for M1 receptors as shown in Tables 2 and 3. In this regard AF150 may be an excellent drug for the treatment of disorders with cholinergic hypofunction such as SDAT since M1 selectivity and high efficacy are believed to be of particular therapeutic value in these type of disorders.

The potency of AF150 (compound #5) (and for comparison other cholinergic compounds) in displacing

TABLE 1

Apparent affinity states for M1 muscarinic receptor in rat cerebral cortex

| Compound # | $K_H(\mu M)$ −G | $K_H(\mu M)$ +G | % H −G | % H +G | $K_L(\mu M)$ −G | $K_L(\mu M)$ +G | % L −G | % L +G | $\frac{K_{L-G}}{K_{H-G}}$ |
|---|---|---|---|---|---|---|---|---|---|
| 1 | 0.23 | * | 36 | * | 12 | 20 | 64 | 100 | 52 |
| 2 | 0.11 | 0.35 | 53 | 2.7 | 6.7 | 4.2 | 47 | 73 | 61 |
| 4 | 0.7–1 | 0.7–1 | * | * | 0.7–1 | 0.7–1 | * | * | 1 |
| 5 | 0.11 | * | 21 | * | 11 | 21 | 83 | 100 | 100 |
| 6 | 3.7 | 4.6 | 39 | 17 | 4.8 | 59 | 61 | 83 | 13 |

*Competition curves were significantly better fitted to a one site-model (mass-action curve).
Notes on Table 1:
$K_i = K_H$ or $K_L = IC_{50}/1 + C/K_D$ where $C = 4.4$ nM is the concentration of the radioactive ligand ($^3$H-PZ) and $K_D = 13.9$ nM is the dissociation constant thereof. $K_H$, $K_L$, % H and % L are the apparent inhibition constants of the tested ligands for the high and low affinity sites, respectively. G is GppNHp (guanylyl imidodiphosphate), and was used in 0.1 mM concentration. Displacement of $^3$H-PZ from cortical binding sites was performed in Tris/Mn buffer (pH 7.4) for one hour at 25° C.; the buffer included 1 mM EDTA and 2 mM Mn$^{++}$ ions. The method is similar to the procedure described by Potter and Ferrendelli (J. Pharmacol. Exptl. Therap. 248: 974–978, 1989). The binding data were analyzed using a GraphPAD program and were fitted to one or two components. Values are means from 1–3 experiments carried out in triplicates.

Surprisingly, AF150 and AF151 show a typical two-affinity states in presence of $^3$H-PZ with a very high $K_L/K_H$ ratio for AF150. Moreover, GppNHp shifted the high-affinity state into the low-affinity state. AF150 and AF15i show both high affinity for M1 putative receptors and a high efficacy on the same receptor. This can be concluded because $^3$H-PZ at the concentrations used (⅓ of its $K_D$) binds only to M1 receptors. The data indicate that both AF150 and AF151 are highly efficacious agonists activating M1 receptors and are expected therefore to activate the transduction mechanism which is involved in secondary messengers coupled to M1 receptors, such as phosphatidyl inositol turnover and $Ca^{2+}$ mobilization for example. Simultaneous activation of both H and L sites may prove to be necessary for functional effects. In this regard, AF150 and AF151 from rat brain homogenates, cerebellum or frontal cortex, the following $^3$H-labelled compounds, namely, (−)$^3$H-quinuclidinyl benzilate ($^3$H-QNB; a non-selective M1 and M2 antagonist) and $^3$H-Pirenzepine ($^3$H-PZ; a selective M1 antagonist), was investigated. For comparison purposes, oxotremorine (an M2>M1 tertiary agonist), oxotremorine-M and carbachol (mixed M2 and M1/M2 quaternary agonists), AF102B (see U.S. Pat. No. 4,855,290) and McN-A-343 (an M1 quaternary agonist) were included. The results are shown in Tables 2 and 3.

TABLE 2

Apparent affinity states for M1 (displacement of $^3$H-PZ from rat cerebral cortex) and for M2 muscarinic receptors (displacement of $^3$H-QNB from rat cerebellum)

| | CORTEX | | | | CEREBELLUM | | | | | | |
| | $^3$H-PZ-Binding | | | | $^3$H-QNB-Binding | | | | | RATIOS | |
| COMPD. # | $K_H$ (a) $\mu M$ | $K_L$ (b) $\mu M$ | % H | % L | $K_H$ (c) $\mu M$ | $K_L$ (d) $\mu M$ | % H | % L | c:a | d:b | b:a |
|---|---|---|---|---|---|---|---|---|---|---|---|
| 1 | 3.4 | 42 | 35 | 55 | 0.60 | 39 | 55 | 45 | 0.18 | 0.93 | 12 |
| 2 | 0.1 | 6.7 | 53 | 47 | 0.069 | 5.2 | 49 | 51 | 0.69 | 0.78 | 67 |
| 4 | 1 | * | 100 | * | 6 | * | 100 | * | 6 | * | * |
| 5 | 0.02 | 18 | 24 | 76 | 4.5 | 79 | 49 | 51 | 225 | 4.4 | 900 |
| 9 | 3.8 | * | 100 | * | 24.4 | * | 100 | * | 6.4 | * | * |

Displacements of $^3$H-PZ and $^3$H-QNB binding were performed in 10 and 50 mM phosphate buffers, respectively. $K_i=K_H$ or $K_L$ were as expressed in Table 1. $K_D$ values for $^3$H-PZ and $^3$H-QNB were 13.9 and 0.093 nM, respectively (Fisher et al, J. Pharmacol. Exptl. Therap., 1991, in the press).

TABLE 3

Apparent affinity states for M1 (displacement of $^3$H-QNB from rat cerebral cortex) and for M2 muscarinic receptors (displacement of $^3$H-QNB from rat cerebellum)

| | CORTEX | | | | CEREBELLUM | | | | | RATIOS | | |
|---|---|---|---|---|---|---|---|---|---|---|---|---|
| | $^3$H-QNB-Binding | | | | $^3$H-QNB-Binding | | | | | | | |
| COMPD. # | $K_{H1}$ (a) | $K_{L1}$ (b) | % | | $K_{H2}$ (c) | $K_{L2}$ (d) | % | | | | | |
| | μM | | H1 | L1 | μM | | H2 | L2 | c:a | d:b | b:a | d:c |
| 1 | 0.6 | 235 | 28 | 72 | 0.75 | 50 | 61 | 39 | 1.25 | 0.21 | 392 | 67 |
| 2 | 0.11 | 37 | 26 | 74 | 0.069 | 5.2 | 49 | 51 | 0.6 | 0.14 | 336 | 75 |
| 3 | 0.016 | 1.6 | 13 | 87 | 0.014 | 0.58 | 35 | 65 | 0.9 | 0.36 | 100 | 41 |
| 4 | 1.8 | * | 100 | * | 5.9 | * | 100 | * | 3.3 | * | * | * |
| 5 | 1.4 | 67 | 13 | 87 | 4.9 | 83 | 51 | 49 | 3.5 | 17 | 49 | 17 |
| 9 | 5.84 | * | 100 | * | 11 | * | 100 | * | 1.9 | * | * | * |

*Competition curves were significantly better fitted to a one site-model (mass-action curve). Note: the K values were generated by a non-linear, least-squares curve fitting of the data using the GRAPHPAD-2 two- and one- site analysis and statistics, as expressed in Table 1.

Displacement of $^3$H-QNB binding ($K_D$ value for $^3$H-QNB of 0.093 nM) was performed in 50 mM phosphate buffer for one hour at 37° C. (Fisher et al, J. Pharmacol. Exptl. Therap., 1991, in the press).

It may be seen from Tables 2 and 3 that AF150 shows high selectivity for M1 muscarinic receptors.

TEST 4

Modification of Muscarinic Agonist Binding to Cortical Membranes by $Cu^{++}$ Treatment Transition metal ions and quanine nucleotides exert strong effects on the affinity of agonists for muscarinic receptors, which probably result from modification in the proportions of the different agonist binding states (Gurwitz and Bokolovsky, Biochem. Biophys. Res. Commun. 96: 1296–1301, 1980; Aronstam et al, Mol. Pharmacol. 14: 575–582, 1978). Addition of $Cu^{++}$ which like certain other transition metal ions are known to form stable coordination complexes with protein sulfhydryl residues, has been shown to increase the apparent affinity of muscarinic agonists by increasing the proportion of high affinity sites and eliminating the sensitivity to quanine nucleotides (Farrar and Hoss, Trans. Am. Soc. Neurochem. 13: 250, 1982; Gurwitz et al, Biochem. Biophys. Res., Commun. 120: 271–276, 1984).

As shown in Table 4, $Cu^{++}$ treatment did not modify the affinity observed for the classical non-selective muscarinic antagonists attopine and scopolamine, as well as for the M1 selective antagonist pirenzepine. On the other hand, binding parameters of the classical non-selective agonists, carbachol and oxotremorine, showed that $Cu^{++}$ treatment increased their apparent affinity, i.e. the competition curves were shifted to lower agonist concentrations. Analysis of the competitive binding data according to a two-site model is summarized in Table 4, and indicates that $Cu^{++}$ treatment increased the proportion of high affinity binding sites from 32 to 51% for oxotremorine and from 25 to 44% for carbachol with no significant changes in their two affinity constants $K_H$ and $K_L$.

The binding parameters for AF102B were also affected by $Cu^{++}$, in that, as shown by the data in Table 4, its interaction with untreated membranes represents binding to a single population of sites with $K_i=3.3$ μM, whereas following $Cu^{++}$ treatment a high affinity binding state was also observed, representing 26% of the total sites with $K_H=0.02$ μM. No change was observed in the low affinity binding constant. Thus, it is shown that AF102B interacts with muscarinic receptors in the cerebral cortex membrane preparation in a fashion typical for agonists, i.e. the receptor-ligand complex may interact with G-protein(s) (c.f. discussion by Gurwitz et al, 1984).

AF150 also exhibited agonistic binding characteristics in these studies. In untreated membranes it showed multiple affinity states (0.32 μM and 33.5 μM for the high and the low affinity sites, respectively). The proportion of the high affinity sites was increased from 14 to 37% following $Cu^{++}$ treatment, suggesting that AF150 might behave as an agonist for cerebral cortex muscarinic receptors.

TABLE 4

$K_i$ values using $(-)^3$H-QNB binding to rat cerebral cortex homogenates with and without $Cu^{++}$ treatment

| | without pretreatment | | | with $Cu^{++}$ pretreatment | | |
|---|---|---|---|---|---|---|
| Agonist # | $K_H$(μM) | $K_L$(μM) | % H* | $K_H$(μM) | $K_L$(μM) | % H* |
| 1 | 0.093 ± 0.07 | 27.0 ± 0.7 | 25 ± 1 | 0.11 ± 0.010 | 17.5 ± 3.2 | 44 ± 3 |
| 3 | 0.02 ± 0.005 | 13.3 ± 1.4 | 32 ± 3 | 0.03 ± 0.001 | 7.2 ± 1.7 | 51 ± 7 |
| 4 | | 3.3 ± 0.6 | 0 | 0.02 ± 0.001 | 3.0 ± 0.01 | 26 ± 5 |
| 5 | 0.32 ± 0.060 | 33.5 ± 1.8 | 14 ± 1 | 0.52 ± 0.003 | 18.0 ± 2.0 | 37 ± 2 |
| 9 | 0.34 ± 0.1 | 8.5 ± 0.8 | 13 ± 5 | 0.18 ± 0.09 | 5.7 ± 0.2 | 30 ± 7 |
| | $K_H$(nM) | $K_L$(nM) | % H* | $K_H$(nM) | $K_L$(nM) | % H* |
| 10 | 19.5 ± 0.5 | 695 ± 5 | 72 ± 3 | 12 ± 2 | 560 ± 60 | 64 ± 6 |
| 11 | | 0.38 ± 0.011 | 0 | | 0.2 ± 0.04 | 0 |
| 12 | | 0.09 ± 0.004 | 0 | | 0.1 ± 0.005 | 0 |

*% of high affinity state.

In the above Table, stated values are means ±SEM of at least 3 experiments; each experiment was performed in triplicate samples. The assay was performed in modified Krebs buffer at pH 7.4 for 2 hours at 25° C. with and without pretreatment for 30 minutes if rat cerebral cortex membranes with $Cu^{++}$ (100 μM)

(Fisher et al, J. Pharmacol. Exptl. Therap., 1991, in the press).

TEST 5

The Effects of Test Compounds on the Expression in Cell Lines of Subtypes of Muscarinic Receptors On the basis of pharmacological data, muscarinic receptors have been divided into three subtypes (M1, M2 and M3). Molecular cloning studies have identified five genetically distinct muscarinic receptor subtypes ($m_1$–$m_5$). Functional expression of these genes has indicated a correlation between the genetically and pharmacologically defined subtypes, where M1≡$m_1$, $m_4$ and $m_5$; M2≡$m_2$; and M3≡$m_3$ (Buckley et al, Mol. Pharmacol. 35: 469–476, 1989).

Stimulation of $m_1$ and $m_3$ receptors elicit dose-dependent increases in the hydrolysis of phosphoinositides (PI). Agonist activation of the $m_1$ receptor also elicits increases in basal and forskolin-stimulated cAMP, whereas the $m_3$ receptor has no effect on intracellular cAMP levels (Buck and Fraser, Biochem. Biophys. Res. Comm. 173: 662–672, 1990). Stimulation of the $m_2$ and $m_4$ receptors by muscarinic agonists leads to preferential inhibition of adenylate cyclase (AC) activity (Mei et al, Life Sciences, 45: 1831–1851, 1989).

The new compounds AF150, AF151 and AF150(S) were assayed for their ability to stimulate PI in CHO cells transfected with $m_1$ and $m_3$ receptors, respectively (Buck and Fraser, loc cit), and in cultured human neuroblastoma cells, line SK-N-SH, which express mainly the $m_3$ subtype, but not the $m_1$ subtype (Pinkas-Kramarski et al, Neurosci. Lett. 188: 335–340, 1990; Luthin et al Mol. Pharmacol. 34: 327–333, 1988). These compounds were also assayed on cultured PC12 cells which express mainly $m_4$ subtype receptors and are coupled to inhibition of AC activity (Pinkas-Kramarski et al, loc cit).

Stimulation of PI breakdown was assayed using the method described by Stein et al (EMBO J. 7: 3031–3035, 1988), and modulation of AC activity was assayed by the method of Stein et al, loc cit and Pinkas-Kramarski et al (FEBS Lett., 239: 174–178, 1988). The results are shown in Table 5 and are compared with carbachol, a full muscarinic agonist (mixed M1/M2 type) and with AF102B.

In Table 5, the agonistic effect on $m_1$ receptors is evidenced by increased PI hydrolysis and AC activity, whereas stimulation of $m_4$ receptors is reflected by inhibition of AC activity; $m_3$ stimulation leads to increased PI hydrolysis. From this Table, it is evident that surprisingly both AF150 and AF151 are full agonists on the $m_1$ and $m_4$ muscarinic receptor subtypes, but partial agonists on the $m_3$ subtypes. In addition, while AF150 and AF151 are full agonists on $m_1$ receptors as evidenced by PI hydrolysis, these compounds differ surprisingly from carbachol as evidenced from their very weak effect on potentiation of AC activity on the same receptors. Thus, carbachol-induced activation of $m_1$ muscarinic receptors elicits increases in basal and forskolin-stimulated cAMP (232–356% and 546–1382%, respectively), yet both AF150 and AF151 are equipotently very weak in this test (33% and 76%, respectively). Thus, these compounds show a unique activity and selectivity and could therefore be particularly useful for the treatment of SDAT (Braan et al, FEBS Lett. 230: 90–94, 1988).

TEST 6

The Effect of Test Compounds on Synaptosomal Acetylcholine (ACh) Release

The effects of AF150 (and for comparison purposes, AF125, MeN-A-343 and oxotremorine) on basal- and $K^+$-evoked release of $^3H$-ACh were studied on synaptosomes prepared from rat cerebral cortex using the methods described in detail by Pittel et al (J. Neurochem., 55: 665–672, 1990). Results are shown in Table 6. Surprisingly, the two closely related structures, AF150 and AF125, had differing effects on $^3H$-ACh release. Thus, while AF125(1 mM) inhibited the $K^+$-evoked release of ACh, AF150(1 mM) surprisingly potentiated it. These results indicate that AF125 acts on presynaptic receptors like oxotremorine, a classical M2 agonist. On the other hand, the action of AF150 on presynaptic muscarinic receptors, causing an increase in $K^+$-evoked ACh release, can be considered either as an M2 antagonistic or an M1 agonistic effect. Hadhazy and Szerb (Brain Res. 123: 311–322, 1977) and Gulya et al (Neurochem. Int. 15: 153–156, 1989) demonstrated that muscarinic antagonists stimulate the $K^+$-evoked ACh release. Suzuki et al (Neurosci. Lett. 84: 209–212, 1988) and Pittel et al, loc cit, showed that muscarinic antagonists can also stimulate the basal ACh release. The latter study suggests that stimulatory muscarinic receptors

TABLE 5

Effects of the test compounds on PI hydrolysis and AC activity in cell cultures expressing $m_1$, $m_3$ and $m_4$ receptor subtypes.

| Compound # | CHO transfected with | | | | SK-N-SH | | PC12 | |
|---|---|---|---|---|---|---|---|---|
| | $m_1$ | | $m_3$ | | $m_3$ | | $m_4$ | |
| | PI | $EC_{50}$ | PI | $EC_{50}$ | PI | $EC_{50}$ | AC | $EC_{50}$ |
| 1 | +++ | 8 | +++ | 5 | +++ | 25 | +++ | 1.5 |
| 4 | +20%[a] | 30[b] | — | [c] | — | [d] | +40%[a] | 0.1[b] |
| 5 | +++ | 13 | +38%[a] | 10[b] | + | 3 | +++ | 1 |
| 6 | +++ | 54 | +45%[a] | 10[b] | NT | | +++ | 1 |
| 7 | +17%[a] | NT | NT | | NT | | NT | |

Notes to Table 5:
$EC_{50}$: effective concentration (μM) at 50% activation
+++ full agonist as compared with carbachol (full agonistic activity was tested for all compounds at 1 mM)
+ partial agonist as compared with carbachol
— no stimulation of PI or inhibition of AC
PI phosphoinositides hydrolysis
AC adenylate cyclase activity expressed by the change in cAMP concentration
NT not tested
[a] % of carbachol effect
[b] effective concentration (μM) which induces the effect
[c] 22 μM AF102B inhibited the effect of 1 mM carbachol
[d] 1 mM AF102B inhibited the effect of 1 mM carbachol that modulate ACh release are present in the CNS and they can be pharmacologically considered of the M1 subtype. The existence of muscarinic autoreceptors that increase ACh release was manifested also in the PNS in smooth muscle preparation (Kilbinger and Nafziger, Naunyn Schmiedebergs Arch. Pharmacol. 328: 304–309, 1985).

TABLE 6

Effects of test compounds on basal and $K^+$-evoked release of acetylcholine (ACh) from rat cerebral cortex synaptosomes.

| Compound # | Concn. mM | Basal $^3$H-ACh release % | $K^+$-evoked $^3$H-ACh release % |
|---|---|---|---|
| 3 | 0.1 | NT | 56 |
| 5 | 0.1 | 121 | 110 |
| 5 | 1.0 | NT | 115 ± 4 (6)* p < 0.01 |
| 5 + 10 | 0.1 10 | 87 | 91 |
| 8 | 1.0 | NT | 78 ± 9 (2)* |
| 9 | 0.1 | 144 | 172 |

Notes to Table 6:
results are from 1–3 experiments unless specified otherwise*
NT = not tested
nM The antagonistic effect of pirenzepine (an M1 antagonist) on the potentiating effects of AF150 on $K^+$-evoked $^3$H-ACh release (as noted from Table 6), could indicate that AF150 can be considered an M1 agonist, which thus activated M1 excitatory autoreceptors. However, regardless of the mechanism of action of AF150, i.e. whether, this can be attributed to, e.g., (a) M1 post- and pre-synaptic agonistic activity, or (b) M1 postsynaptic agonistic and an M2 pre-synaptic antagonistic effect, this compound could be especially promising for the control of SDAT and related disorders.

TEST 7

Electrophysiological Evaluation of AF150 in Rat Hippocampal Slices

Acetylcholine (ACh) has a number of effects in mammalian brain. The main effects were observed in the hippocampal slice and include:
(1) a blockade of sustained outward potassium ($K^+$) current activated by depolarization ($I_M$);
(2) a blockade of $Ca^{++}$-dependent $K^+$ current underlying the slow after hyperpolarization (AHP);
(3) a blockade of sustained $K^+$ current at rest;
(4) a transient outward $K^+$ current;
(5) reported effects of ACh on postsynaptic potentials (an increase in spontaneous and decrease in evoked ones) and on $Ca^{++}$ currents.
(Segal, Brain Res. 452: 79–98, 1988; Duttar and Nicoll, J. Neurosci. 8: 4214–4224, 1988.)

The results using gallamine (an M2 antagonist) and pirenzepine (PZ, an M1 antagonist), suggest that an M2 receptor could mediate the depression of EPSP and blockade of $I_M$. In contrast, the depolarization and the blockade of the AHP, insensitive to gallamine and blocked by 0.3 µM of PZ, are likely to be mediated by M1 receptors (Duttar and Nicoll, loc cit).

In general terms the effects of microdrops of AF150, ACh and PZ were applied to rat hippocampal cells recorded intracellularly. The exact concentrations of the drug at the receptor sites are not known, using this method. However, this method has an advantage over the perfusion method, in that it gives a more correct picture from the electrophysiological point of view (Segal, loc cit).

Intracellular responses to AF150 of CA1 neurons in the hippocampal slice were recorded, using the method of Segal. Small hyperpolarizing current pulses (current traces not shown) were alternated with stimulation of the Schaffer-commissural afferents producing postsynaptic potentials. AF150 applied topically, by microdrops (100 µM) caused a potent depolarizing response. Hyperpolarizing the cell to control potentials, reveals a real increase in input resistance at rest. AF150 blocks the slow AHP mediated by a $Ca^{++}$-dependent $K^+$ conductance. AF150 causes a small reduction in postsynaptic potentials (PSPs). Pirenzepine (10 µM, an M1 muscarinic antagonist) markedly reduced the depolarization caused by AF150. The increase in input resistance at rest, was also prevented by pirenzepine. The blockade of the slow AHP by AF150 was markedly reduced in pirenzepine-treated slices. The reduction in PSPs cause by AF150 was unaffected by pirenzepine.

CONCLUSIONS (1) AF150 causes depolarization, increased input resistance, and blocks the slow AHP, which effects are antagonized by the M1 receptor antagonist pirenzepine; however, an effect on PSPs which was small compared to ACh was detected and was unaffected by pirenzepine.

(2) Surprisingly, AF150 appears to be a more specific agonist for M1 receptors than for M2 receptors.

(3) When compared with AF102B, it is clear that AF150 is far more efficacious and causes a depolarization (blocked by pirenzepine) which is not shown in the case of AF102B. Both AF150 and AF102B block the slow AHP (pirenzepine-sensitive M1 effect).

TEST 8

Pharmacodynamic Profile and General Toxicity

1. Objective:
The objective of this study was to establish the primary pharmacodynamic profile and to evaluate the general toxicity of AF150. The study was carried out by observing mice after injection at 3 dose levels of AF150.

2. Materials and Methods:
   a. Animals: Mice, Male CD strain, 20–30 g.
   b. Group size: n=5.
   c. Route of administration: Intraperitoneal (i.p.).
   d. Dose levels: 1, 5 and 10 mg./kg.
   e. Volume of dosage: 10 ml./kg.
   f. Preparation of Test Material: AF-150 was dissolved in saline solution.
   g. AF150 at 3 dose levels was administered i.p. to mice (n=5). Behavioral changes up to two hours after dosing were recorded as well as additional observations up to 24 hours administration for death occurrence. Analgesic effects were evaluated by the tail pinch method at 15, 30, 60 and 120 minutes post dosing. Except for analgezia, animals were observed for the following effects: the occurrence of tremors, convulsions, respiratory distress, salivation, diarrhea, changes in pupil diameter, exaphthalamus, motor coordination, hypo- or hyperactivity and vocalization.

EXPERIMENTAL RESULTS 1 mg./kg. i.p.: Very slight salivation and diarrhea was observed for about 30 minutes after injection. No analgesia was seen at any of the times of observation. No other central or autonomic effects were observed.

5 mg./kg. i.p.: Decreased motor activity was observed up to 60 minutes after administration, then normal activity was regained. Partial analgesia was seen 15 minutes after injection. Motor coordination was reduced up to 30 minutes after injection. Mydriasis was observed 5 minutes after injection. Slight salivation and diarrhea was seen from 10 to 60 minutes after injection.

10 m.g/kg. i.p.: Complete hypoactivity was observed from 5 to 75 minutes in 2 of the animals, the other 3 regained their activity after 120 minutes. Slight tremors were observed 10 minutes after injection for a short period. Motor coordination was markedly affected throughout the 2 hours of observation. Analgesia was complete at 15 and 30 minutes after injection; no analgesia was seen at $\geq 60$ minutes. Moderate salivation, diarrhea, lacrimation and mydriasis were observed 5 minutes after injection and became severe 10 minutes after injection, but severity declined and all signs were absent 90 minutes after injection.

TEST 9

The effects of AF150 in AF64A-Treated Rats in a Passive Avoidance (PA) Paradigm

This animal model mimics to a certain extent the cholinergic hypofunction in SDAT (Fisher and Hanin, Ann. Rev. Pharmacol. Toxicol. 26: 161–182, 1986). The method described in Fisher et al (J. Pharmacol. Exptl. Therap., 1991, in the press) and in Fisher et al (Neurosci. Lett. 10.2: 325–331, 1989) was used here. The results are shown in Table 7.

As may be seen from the Table, AF150 was beneficial in this animal model at all three doses tested, by i.p. injection. In addition. AF150 (in free base form) improved significantly the retention latency of A64A-treated rats when it was administered orally at 0.2 and 1.0 mg./kg. (not shown). The latter finding indicates that the compound is well absorbed and effective when administered orally, at very low doses. Notably, the low effective doses in the PA test are free of overt side effects. Thus, AF150 has a wide safety margin, as evidenced in learning and memory tests like PA.

No significant differences were found among the different groups of animals tested in the initial latency test; the initial latency ranged from 20 and 31 seconds. In all the experiments using AF150, the compound as free base was dissolved in 10 mM phosphate buffer having pH 7.35.

Significant interaction when $F(2.54)=6.33$, $p<0.005$. By analyzing the foregoing data according to Scheffe's main contrasts, the following significant results were found:

($p<0.005$) AF150 (0.1 mg./kg.) vs. AF64A-buffer
($p<0.025$) A64A-AF150(0.2 mg./kg.) vs. AF64A-buffer
($p<0.001$) A64A-AF150(1.0 mg./kg.) vs. AF64A-buffer
($p<0.05$) A64A-AF150(1.0 mg./kg.) vs. AF64A-AF150(0.2 mg./kg.)
($p<0.05$) saline-buffer vs. AF64A-buffer
($p<0.005$) saline-buffer vs. AF64A-AF150(1.0 mg./kg.)
($p<0.025$) saline-buffer vs. saline-AF150(1.0 mg./kg.)

TEST 10

The Effects of AF150 in AF64A-Treated Rats in an 8-Arm Radial Maze (RAM) Paradigm This animal model mimics the cholinergic hypofunction and cognitive dysfunction in SDAT (Fisher and Hanin, loc cit; Fisher et al, Neurosci. Lett. 102: 325–331, 1989); the method described in the latter publication was used here. In brief, saline- and A64A-pretreated rats (3 mmole/2 µl./side, icv) were used in these experiments, 2.5 months after the lesion. The experiment was carried out over a three-week period. During the first week the rats were trained to find food pellets in all eight arms of the maze. After learning the task, the rats were trained using the delay procedure. During a pre-delay session, four of the arms of the maze were closed and the rats collected the food pellets from the remaining four opened arms. During this period working memory errors were recorded. Following a two hour delay, the rats were returned to the maze. All of the arms of the maze were now open but only four of them, those which were closed during the pre-delay session were baited. The rats had to collect the food pellets without entering any previously visited arms, whether during the pre-delay or the post-delay session. After reaching a baseline level the rats were tested for their performance during the third week of the experiment in which either 10 mM phosphate buffer (pH 7.3), or AF150 (0.07 or 1.0 mg./kg. free base dissolved in 10 mM phosphate buffer, pH 7.3), were administered i.p., immediately after the pre-delay session, once a day for five days. The results were listed according to the week (II or III), and are shown in Table 8.

TABLE 7

Passive avoidance studies on AF150

| | Retention latency (secs.) after 72 hours | | | |
|---|---|---|---|---|
| | 10 mM phosphate buffer | AF150 (mg./kg., i.p.) | | |
| | | 0.1 | 0.2 | 1.0 |
| Rats treated with saline | 438.1 ± 57.0 | 511.8 ± 45.7 | 479.1 ± 57.2 | 571.6 ± 28.4 |
| Rats treated with AF64A* | 174.8 ± 44.2 | 449.5 ± 52.1 | 481.1 ± 54.3 | 600.0 ± 0 |

*3 nmole/2 µl./side, icv

TABLE 8

| | Working memory errors (session I) | | | | | |
|---|---|---|---|---|---|---|
| | phosphate buffer | | AF150 (mg./kg., i.p.) | | | |
| | | | 0.07 | | 1.0 | |
| | (pre)II | III | (pre)II | III | (pre)II | III |
| Sal. | 0.27 ± 0.11 | 0.27 ± 0.09 | 0.33 ± 0.12 | 0.18 ± 0.07 | 0.11 ± 0.05 | 0.13 ± 0.07 |
| AF64A | 3.51 ± 0.74 | 9.02 ± 2.59 | 3.33 ± 1.18 | 3.75 ± 1.04 | 3.00 ± 0.94 | 4.22 ± 1.76 |

Sal. = saline

The working memory errors increased during the pre-delay session in the group of AF64A+buffer treated rats; it seems that as the learning process progresses, such rats became more confused, perhaps because a previous experience does not facilitate, but rather interferes with, the following one. AF150 at the tested doses (0.07 or 1.0 mg./kg., i.p.) was significantly beneficial in consolidating the working memory (in the pre-delay session only) of the AF64A treated rats; in fact, the lower dose of 0.07 mg./kg., i.p., is slightly better than the higher tested dose. The beneficial effect of AF150 in this experiment is the prevention of deterioration in AF64A treated rats, rather than simply improvement. AF150 had no improving effect on the working memory errors during the post-delay session, although those errors also increased during that period. The reasons for this effect could be: (a) the pre-delay session is s more simple task than the post-delay session, therefore demanding less cognitive ability and being easier to improve; (b) AF150 was administered after the pre-delay session, therefore improving the consolidation of the memory traces of the four first entries. It is possible that this post-administration of the drug had no effect on the post-delay session, namely on the learning of the other four entries, which can be a different cognitive process.

These results, taken together with the results of AF150 in the PA test, would seem to indicate that this compound is a very potent cognitive activator, surprisingly more potent than AF102B. Therefore, AF150 can be especially promising for the control of SDAT.

TEST 11

The effects of AF151 in AF64A-Treated Rats in the Morris Water Maze (MWM) Paradigm This animal model, which mimics the cholinergic hypofunction and cognitive impairments in SDAT was used as described in Fisher et al (J. Pharmacol. Exptl. Therap, 1991, in the press).

Rats were injected with AF64A (3 mmole/2 μl./side, icv) or saline (2 μl., icv), in presence of phosphate buffer or AF151. The results, in terms of the path length (cm.) travelled by the rats are shown in Table 9.

AF151 at all three dosage rates showed a significant dose dependent beneficial effect in restoring cognitive dysfunction in the A64A treated rats. Thus, AF151 can be a promising drug in the treatment of SDAT, since it is effective at very low doses without exhibiting overt side effects.

The statistical significance of the data recorded in Table 9 is as follows:

AF151 (1.0 mg./kg., i.p.) vs. AF64A+phosphate buffer: $p<0.01$

AF151 (0.3 mg./kg., i.p.) vs. AF64A+phosphate buffer: $p<0.05$

AF151 (0.07mg./kg., i.p.) vs. AF64A+phosphate buffer: $p<0.07$.

TABLE 9

| icv | Treatment | Path length (cm.) travelled by rats in MWM | | | | |
|---|---|---|---|---|---|---|
| | | Block | | | | |
| | | 1 | 2 | 3 | 4 | Reversal |
| AF64A | phosphate buffer* | 831.5 ± 100.8 | 1040.2 ± 188.7 | 340.6 ± 41.6 | 582.6 ± 84.7 | 606.6 ± 78.9 |
| | AF151 | | | | | |
| | 0.07 | 729.0 ± 98.2 | 918.1 ± 124.3 | 743.1 ± 151.1 | 574.9 ± 101.1 | 602.9 ± 97.9 |
| | 0.3 | 862.3 ± 151.0 | 843.5 ± 197.5 | 539.9 ± 146.2 | 297.9 ± 60.4 | 390.5 ± 77.0 |
| | 1.0 | 656.6 ± 107.6 | 802.7 ± 111.1 | 795.0 ± 131.3 | 434.4 ± 33.0 | 606.0 ± 60.0 |
| Sal. | phosphate buffer* | 622.2 ± 71.1 | 558.7 ± 69.6 | 314.3 ± 41.7 | 282.1 ± 41.4 | 433.2 ± 93.3 |
| | AF151 | | | | | |
| | 0.07 | 490.6 ± 74.0 | 562.9 ± 92.7 | 429.2 ± 76.5 | 278.0 ± 44.0 | 453.9 ± 76.0 |
| | 0.3 | 517.8 ± 45.3 | 365.1 ± 58.4 | 424.6 ± 92.3 | 346.7 ± 64.4 | 306.8 ± 43.3 |
| | 1.0 | 607.4 ± 90.6 | 440.2 ± 90.1 | 408.1 ± 97.1 | 233.8 ± 30.6 | 450.0 ± 93.5 |

Sal. = saline
*0.2 ml./kg., i.p.
mg./kg., i.p.
Notes to Table 9:
In brief (c. f. Fisher et al, J. Pharmacol. Exptl. Therap. 1991, in the press), training was continued for five consecutive days, with each rat receiving four trials on each day; results are expressed as blocks (e.g. of four trials/day). During trials 1–16 (days 1–4, training stage) the platform was located in the center of the north-west quadrant of the pool. During trial no. 17, on the fifth day, the platform was removed from the pool entirely (a transfer test). In this trial the rat was placed in the water for a limited period (60 secs.) and its spacial bias was measured. During trials 18–21 on the fifth day the platform was moved to the center of the south-east quadrant (a reversal test). Four starting locations were used: north, south, east or west around the pool's perimeter. The sequence of the locations was semirandomly changed each day. AF151 and phosphate buffer were administered once a day for five days, 30 minutes before testing. The experiment was performed using a tracking system consisting of an image analyzer (cis-2) coupled to a microcomputer (8 MZHz - IBM AT, Galai Laboratories, Ltd.)

While certain embodiments of the invention have been particularly described, it will be apparent to those skilled in the art that many modifications and variations may be made. The invention is accordingly not to be construed as restricted to such embodiments, rather its concept, scope and spirit are to be understood having regard to the claims which follow.

We claim:

1. A compound selected from the group consisting of
1-methylpiperidine-4-spiro-4'-(2'-methyl-1',3'-oxazoline),
1-methylpiperidine-4-spiro-4'-(2'-ethyl-1',3'-oxazoline),
2-methylspiro(1,3-oxazoline-5,4')-1'-methylpiperidine,
2-methylspiro(1,3-thiazoline-5,4')-1'-methylpiperidine,
2-ethylspiro(1,3-oxazoline-5,4')-1'-methylpiperidine,
including the pharmaceutically acceptable acid addition salts thereof.

2. A compound selected from the group consisting of
1-methylpiperidine-4-spiro-4'-(2'-methyl-1',3'-oxazoline),
1-methylpiperidine-4-spiro-4'-(2'-ethyl-1',3'-oxazoline),
2-methylspiro(1,3-oxazoline-5,4')-1'-methylpiperidine,
2-methylspiro(1,3-thiazoline-5,4')- 1'-methylpiperidine,
2-ethylspiro(1,3-oxazoline-5,4')- 1'-methylpiperidine,
including the acid pharmaceutically acceptable addition salts thereof.

3. A pharmaceutical composition for use in treating diseases of the central and peripheral nervous system in mammals, which comprises an amount effective for use in treating said diseases, of a member of the group consisting of
1-methylpiperidine-4-spiro-4'-(2'-methyl-1',3'-oxazoline),
1-methylpiperidine-4-spiro-4'-(2'-ethyl-1',3'-oxazoline),
2-methylspiro(1,3-oxazoline-5,4')-1'-methylpiperidine,
2-methylspiro(1,3-thiazoline-5,4')-1'-methylpiperidine,
2-ethylspiro (1,3-oxazoline-5,4')-1'-methylpiperidine,
including the acid pharmaceutically acceptable addition salts thereof;
together with an inert carrier or diluent.

4. A method for treating diseases due to a deficiency in the central cholinergic system in mammals, which comprises administering to the mammal a pharmaceutical composition comprising an amount effective for use in treating said diseases, of a member of the group consisting of
1-methylpiperidine-4-spiro-4'-(2'-methyl-1',3'-oxazoline),
1-methylpiperidine-4-spiro-4'-(2'-ethyl-1',3'-oxazoline),
2-methylspiro(1,3-oxazoline-5,4')-1'-methylpiperidine,
2-methylspiro(1,3-thiazoline-5,4')-1'-methylpiperidine,
2-ethylspiro(1,3-oxazoline-5,4')-1'-methylpiperidine,
including the acid addition salts thereof; together with an inert carrier or diluent.

* * * * *